United States Patent
Chamorro Sanchez

(10) Patent No.: US 10,709,710 B2
(45) Date of Patent: Jul. 14, 2020

(54) COMPOSITION COMPRISING URIC ACID FOR THE TREATMENT TREATED WITH MECHANICAL THROMBECTOMY

(71) Applicants: Hospital Clinic de Barcelona, Barcelona (ES); Institut D'Investigacions Biomediques Augusti Pi I Sunyer (IDIBAPS), Barcelona (ES)

(72) Inventor: Angel Chamorro Sanchez, Barcelona (ES)

(73) Assignees: HOSPITAL CLINIC DE BARCELONA, Barcelona (ES); INSTITUT D'INVESTIGACIONS BIOMEDIQUES AUGUSTI PI I SUNYER (IDIBAPS), Barcelona (ES)

(*) Notice: Subject to any disclaimer, the term of this patent is extended or adjusted under 35 U.S.C. 154(b) by 275 days.

(21) Appl. No.: 15/752,363

(22) PCT Filed: May 9, 2017

(86) PCT No.: PCT/ES2017/070290
§ 371 (c)(1),
(2) Date: Feb. 13, 2018

(87) PCT Pub. No.: WO2018/206826
PCT Pub. Date: Nov. 15, 2018

(65) Prior Publication Data
US 2020/0009150 A1 Jan. 9, 2020

(51) Int. Cl.
| | | |
|---|---|---|
| *A61K 31/522* | (2006.01) | |
| *A61P 25/00* | (2006.01) | |
| *A61K 9/00* | (2006.01) | |
| A61K 31/7068 | (2006.01) | |
| A61K 38/49 | (2006.01) | |

(52) U.S. Cl.
CPC .......... *A61K 31/522* (2013.01); *A61K 9/0019* (2013.01); *A61P 25/00* (2018.01); *A61K 31/7068* (2013.01); *A61K 38/49* (2013.01)

(58) Field of Classification Search
CPC .............................. A61K 31/70; A61K 31/522
See application file for complete search history.

(56) References Cited

FOREIGN PATENT DOCUMENTS

| | | |
|---|---|---|
| WO | 96/27380 A1 | 9/1996 |
| WO | 2010/112113 A1 | 10/2010 |
| WO | WO2010112113 | * 10/2010 |

OTHER PUBLICATIONS

Romanos et al. Journal of Cerebral Flow and Metabolism, 2007, 27: 14-20.*
International Search Report dated Nov. 9, 2017 for PCT/ES2017/070290.
Amaro Sergio et al: "A pilot study of dual treatment with recombinant tissue plasminogen activator and uric acid in acute ischemic stroke." STROKE; A Journal of Cerebral Circulation Jul. 2007 LNKD—Pubmed: 7525395, vol. 38, No. 7, Jul. 2007 (Jul. 2007), pp. 2173-2175, XP002585040 ISSN: 1524-4628 * abstract.
Romanos Eduardo et al: "Uric acid reduces brain damage and improves the benefits of rt-PA in a rat model of thromboembolic stroke." Journal of Cerebral Blood Flow and Metabolism : Official Journal of the International Society of Cerebral Blood Flow and Metabolism Jan. 2007 LNKDPUBMED: 16596120, vol. 27, No. I, Jan. 2007 (Jan. 2007), pp. 14-20, XP002585041 ISSN: 0271-678X* abstract.
Chamorro Angel et al: "Uric acid therapy improves the outcomes of stroke patients treated with intravenous tissue plasminogen activator and mechanical thrombectomy.", International Journal of Stroke: Official Journal of the International Stroke Society Jun. 2017, vol. 12, No. 4, Dec. 20, 2016 (Dec. 20, 2016), pp. 377-382. XP009501158, ISSN: 1747-4949, DOI: 10.1177/1747493016684354 p. 378, left-hand column; figure 1 figures 1-3; table 1 p. 381, left-hand column, paragraph 2-paragraph 3.
Chamorro Angel et al: "Uric acid administration for neuroprotection in patients with acute brain ischemia. "—Medical Hypotheses 2004 LNKDPUBMED: 14962621, vol. 62, No. 2, 2004, pp. 173-176, XP002585039 ISSN: 0306-9877 * abstract.
Chamorro Angel et al: "Uric Acid Therapy in Stroke Patients Treated With Mechanical Thrombectomy: An Exploratory Analysis of the Uricoictus Trial" The 2nd European Stroke Organisation Conference 2016; May 11, 2016 Barcelona, Spain.

* cited by examiner

*Primary Examiner* — Rei Tsang Shiao
(74) *Attorney, Agent, or Firm* — Lucas & Mercanti, LLP

(57) ABSTRACT

The present invention refers to a composition comprising uric acid for its use in the treatment of brain stroke in a patient treated by means of mechanical thrombectomy.

13 Claims, 1 Drawing Sheet

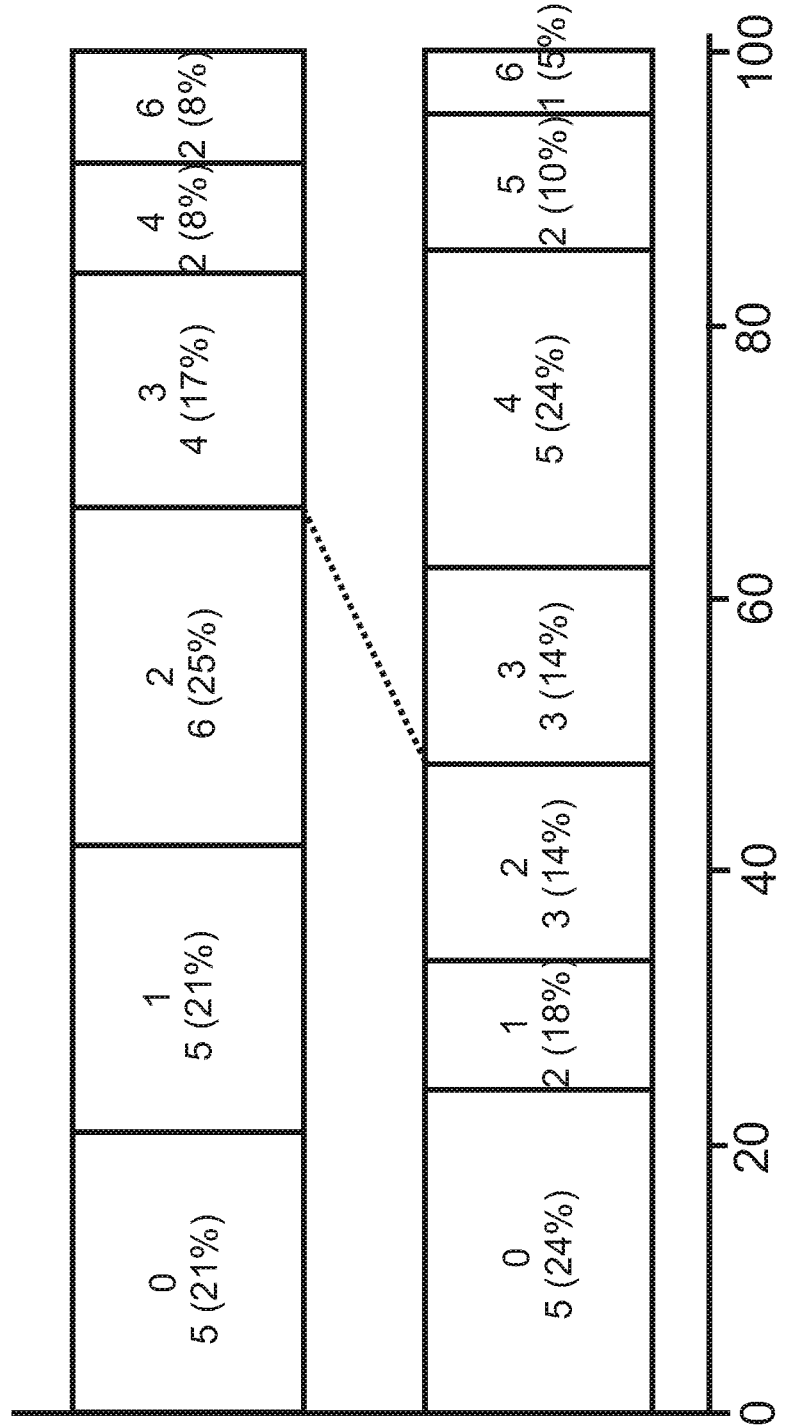

COMPOSITION COMPRISING URIC ACID FOR THE TREATMENT TREATED WITH MECHANICAL THROMBECTOMY

CROSS REFERENCE TO RELATED APPLICATION

This Application is a 371 of PCT/ES2017/070290 filed on May 9, 2017, which is incorporated herein by reference.

FIELD OF THE INVENTION

The present invention refers to the field of biomedicine, more particularly to the treatment of brain stroke and, even more particularly, to the treatment of brain stroke within a specific subgroup of patients, those patients of brain stroke that have been treated or are treated by means of mechanical thrombectomy.

BACKGROUND OF THE INVENTION

Cell death after a cerebrovascular accident or brain stroke is the result of the complex interaction of excitotoxicity, acidosis, inflammation, oxidative stress, peri infarct depolarization and apoptosis.

The term apoptosis is used as a synonym of programmed cell death (hereinafter, PCD); however, apoptosis was originally defined as a set of morphological changes which occur after PCD. In developing neurons, these changes include condensation and excision of chromatin and the formation of the so-called apoptotic bodies. These changes are different from the morphological changes which characterize the inflammation caused by necrosis of the cytoplasmic organelles and the breaking of the mitochondrial and cytoplasmic membrane.

A mild ischemic injury normally induces cell death through an apoptotic-like mechanism instead of through necrosis. Apoptosis activators include oxygen free radicals, linking with death receptors, DNA damage, protease activation and ionic balance disadjustment. Several experimental studies have shown that the inhibition of apoptosis reduces the seriousness of the ischemic lesion.

The activation of caspases is a consequence of mitochondrial apoptosis. The mitochondrial dysfunction and the opening of the mitochondrial transitory permeability pore can result in activation of caspases through the exit of cytochrome C towards the cytoplasm; however, there are other different mechanisms through which mitochondrial dysfunction can contribute to ischemic neuronal death. The seriously damaged mitochondria can be incapable of maintaining the electrochemical gradient necessary for breathing and glucose oxidation. In this way, the mitochondrial dysfunction can aggravate the ischemic injury by exacerbation of the energetic failure. The dysfunctional mitochondria also produces oxygen free radicals which injure other cell organelles and DNA. Therefore, the treatments preventing mitochondrial dysfunction could also be a more powerful neuroprotective strategy than caspase inhibition.

High levels of intracellular $Ca^{2+}$, $Na^+$ and ADP make the mitochondria produce harmful levels of oxygen reactive species. Unlike other organs, the brain is particularly vulnerable to oxygen reactive species since the neurons have relatively low levels of endogenous antioxidants. The abundance of oxygen radicals causes the destruction of cell macromolecules and they participate in signaling mechanisms which produce apoptotic cell death. Ischemia activates nitric oxide synthase (hereinafter, NOS) and increases the generation of nitric oxide (hereinafter, NO), which is combined with super oxide to produce peroxynitrite, a powerful oxidation agent. The production of NO and oxidative stress are also linked to the over activation of poly (ADP-ribose)polymerase-1 (hereinafter, PARP-1), an enzyme for DNA repair.

After the reperfusion, there is an increase in the production of super oxide, NO and peroxynitrite. The formation of these radicals in the proximity of blood vessels plays an important role in the injury induced by reperfusion. These radicals activate the metalloproteases (hereinafter, MMP), which degrade collagen and laminins in the basal lamina, break the integrity in the vascular wall and increase permeability of the hematoencephalic barrier (hereinafter, HEB). Oxidative and nitrosilative stress also activate the recruiting and migration of neutrophils and other leucocytes to the brain vasculature, which release enzymes which additionally increase degradation in the basal lamina and vascular permeability. These events can produce a parenchymatous haemorrhage, vasogenic cerebral oedema and leukocyte infiltration inside the brain.

Uric acid is a potent antioxidant which blocks the reaction between superoxide anion and nitric oxide, which damages the cells when nitrosylating thyroxine residues of proteins. Plasmatic concentration of uric acid is almost 10 times higher than that of other antioxidant substances, such as vitamins C or E, and its antioxidant capacity is higher. Besides, uric acid prevents the degradation of extra cellular superoxide dismutase, which is an essential enzyme for normal endothelial functioning. In culture of hippocampus cells, uric acid protects against excitotoxic damage by glutamate, stabilizing calcium homeostasis and preserving the mitochondrial function. Uric acid has also shown the inhibition of the Fenton reaction.

In an adult rat, the administration of uric acid 24 hours before the occlusion of the middle cerebral artery or 1 hour after the reperfusion significantly reduces the resulting cerebral infarction, suppresses reactive oxygen species accumulation and reduces lipid peroxidation (Yu Z F, et al. *Uric acid protects neurons against excitotoxicf and metabolic insults in cell culture, and against focal ischemic brain injury in vivo*; J Neurosci Res 1998; 53:613-25). Uric acid administration is neuroprotective in a thromboembolism model of focal cerebral ischemia of a rat and this neuroprotective effect is synergic with respect to the beneficial effect attained by rtPA (Romanos E, Planas A M, Amaro S, Chamorro A. *Uric acid reduces brain damage and improves the benefits of rt-PA in a rat model of thromboembolic stroke*. J Cereb Blood Flow Metab. 2007; 27:14-20).

There are studies which show the existing relation between higher levels of uric acid in blood in the moment of a brain stroke and a reduced neurological seriousness caused by said brain stroke.

In addition, the recent study URICO-ICTUS (Clinical study phase 2b/3) showed that the use of uric acid in combination with the standard thrombolytic treatment (alteplase) is safe. Nevertheless, in this study the combined therapy did not show an statistically significant effect and, hence, the conclusion of the study is that no change was seen in the proportion of patients with excellent results at 90 days (Chamorro A, Amaro S, Castellanos M, Segura T, Arenillas J, Martí-Fábregas J, Gállego J, Krupinski J, Gomis M, Cánovas D, Carné X, Deulofeu R, Román L S, Oleaga L, Torres F, Planas A M; URICO-ICTUS Investigators. *Safety and efficacy of uric acid in patients with acute stroke (URICO-ICTUS): a randomised, double-blind phase 2b/3 trial*. Lancet Neurol. 2014; 13:453-60).

Finally, the PCT Patent application WO2010112113 discloses the combined use of uric acid and citicoline for the treatment of ictus, demonstrating their effects in cell cultures models of ischemia.

Therefore, given the complexity of the treatment of brain stroke and the absence of a therapy that allows its effective treatment, there is still a need to investigate in new therapies or combinations thereof that allow an increase not only in the survival rate of the patients of brain stroke but also, and more importantly, that allow to improve the conditions in which such patients survive (increasing their functional independence, reducing brain damage, etc.).

The inventor of the present invention, after extensive and exhaustive research, have surprisingly seen that the administration of uric acid in patients with brain stroke that are or have been treated by means of mechanical thrombectomy shows a synergistic effect and allows to improve the positive results obtained in said patients, drastically and significantly improves the outcome of the patients, increase their functional independence and decrease the damaged brain area., contributing, hence, to solve the problem present in the state of the art and mentioned above.

DESCRIPTION OF THE INVENTION

Therefore, in a first aspect, the present invention refers to a composition comprising uric acid for use in the treatment of brain stroke in patients of said disease that are or have also been treated by means of mechanical thrombectomy.

In a second aspect, the present invention refers to the use of a composition comprising uric acid for the manufacture of a medicament for the treatment of brain stroke in patients of said disease that are or have also been treated by means of mechanical thrombectomy.

In a final aspect, the present invention refers to a method for the treatment of a patient suffering from brain stroke comprising administering a composition comprising uric acid, wherein the patient is a patient of brain stroke treated by means of mechanical thrombectomy and wherein the treatment provides for synergistic effect in the treatment for brain stroke.

As used in the present document "brain stroke", "ictus" and "cerebrovascular accident" are used interchangeably and in an equivalent way and refer to any pathology or clinical situation which implies that a part of the brain stays without blood flow.

As used in the present document, the mention to "uric acid" includes pharmaceutically acceptable salts and any other formulation or chemical form thereof that, once administered to a patient, provides uric acid.

As used in the present document "patient" and it plural are used to refer to mammals, preferably humans, that suffer brain stroke, independently to their sex and age and independently if they have other diseases (diagnosed or not).

Therefore, as noted above, in a first aspect, the present invention refers to a composition comprising uric acid for use in the treatment of brain stroke, characterized in that the patient is a brain stroke patient treated by means of mechanical thrombectomy.

The composition comprising uric acid mentioned above, shows a synergistic effect in the treatment of brain stroke in the group of patients mentioned above, this is, brain stroke patients treated by means of mechanical thrombectomy.

It is contemplated that the brain stroke is ischemic or haemorrhagic. In a preferred embodiment, the brain stroke is an ischemic brain stroke.

It is contemplated that the composition comprising uric acid is used before, during or afterwards the mechanical thrombectomy (this is, to the patient being treated with said technique). Preferably, the composition comprising uric acid is used when the patient is treated by means of mechanical thrombectomy. In the most preferred embodiment, the composition comprising uric acid is used or administered before beginning the mechanical thrombectomy and before ending the infusion of said composition the mechanical thrombectomy is started.

It is contemplated that the mechanical thrombectomy is performed with any stent known in the state of the art and suitable for use with said technique. In a preferred embodiment, the stent used in the mechanical thrombectomy is a first generation stent, more preferably, the stent used in the mechanical thrombectomy is of the type of the Merci clot retrieval device (Concentric medical, Mountain View, Calif.), the Penumbra thromboaspiration system (Penumbra, Inc. Alameda, Calif.), balloon-mounted stents, self-expanding stents and/or retrievable stents, even more preferably the stent used in the mechanical thrombectomy is a retrievable stent, for example, the retrievable stent is Solitaire (ev3 Inc., Irvine, Calif.), Trevo (Concentric Medical, MountainView, Calif.), Solitaire FR, Pulse (Penumbra, Inc., Alameda, Calif.) or Revive (Codman Neurovascular, San Jose, Calif.). In the most preferred embodiment, the stent used in the mechanical thrombectomy is the retrievable stent Solitaire (ev3 Inc., Irvine, Calif.).

It is contemplated that the composition comprising uric acid is used alone or in combination with other compounds. In a preferred embodiment, the composition comprising uric acid is used in combination with a thrombolytic agent, more preferably with a tissue plasminogen activator (hereinafter, tPA) (for example, alteplase).

It is also contemplated that the composition comprising uric acid is used in combination with, for example, citicoline.

In connection with what has been pointed out, it is contemplated that the combined use is within the same composition (this is, that the composition comprising uric acid additionally comprises other components such as tPA, citicoline or combinations thereof) or in the form of at least one additional composition. In the latter, it is contemplated that the composition comprising uric acid is administered before, at the same time or afterwards that the at least one additional composition.

In a preferred embodiment, the composition comprising uric acid is used in combination with a composition comprising tPA (preferably, alteplase) and both compositions are used jointly, this is, they are administered jointly, more preferably, firstly the composition comprising tPA is administered and, before finalizing the administration thereof the administration of the composition comprising uric acid is started.

The amount of uric acid in the composition is a therapeutically effective amount.

In a preferred embodiment, the dose or amount of uric acid is between 250 mg and 1250 mg, more preferably the dose or amount of uric acid is between 500 mg and 1000 mg, even more preferably the dose or amount of uric acid is 1000 mg.

In another preferred embodiment, the concentration of uric acid in the composition is between 1 mg/ml and 4 mg/ml, more preferably 2 mg/ml.

It is contemplated that the acid uric comprised in the composition, is obtained, generated or produced in accordance with any of the methods known in the state of the art. In a preferred embodiment, the uric acid is obtained by chemical synthesis.

The composition comprising uric acid can be presented in any pharmaceutically acceptable form and adapted to the elected route of administration. In this sense, the composition comprising uric acid can comprise pharmaceutically acceptable vehicles and excipients known in the state of the art. In a preferred embodiment, the composition comprising uric acid comprises a pharmaceutically acceptable liquid vehicle, more preferably said liquid vehicle is physiological serum and, even more preferably, said physiological serum comprises 0.1% of lithium carbonate and 5% mannitol.

It is contemplated that the composition comprising uric acid is a slow release composition, an immediate release composition or combinations thereof.

The composition comprising uric acid (and any of the optional at least one additional composition mentioned previously) can be administered by any of the routes known in the state of the art. In a preferred embodiment, the composition comprising uric acid is administered intravenously.

In a second aspect, as noted above, the present invention refers to the use of a composition comprising uric acid for the manufacture of a medicament for the treatment of brain stroke characterized in that the patient is a brain stroke patient treated by means of mechanical thrombectomy.

In the use of the composition comprising uric acid of the present invention (this is, the use in accordance to what has been indicated above), the composition comprising uric acid mentioned above, shows a synergistic effect in the treatment of brain stroke in the group of patients mentioned above, this is, brain stroke patients treated by means of mechanical thrombectomy.

It is contemplated that the brain stroke is ischemic or haemorrhagic. In a preferred embodiment, the brain stroke is an ischemic brain stroke.

It is contemplated that the composition comprising uric acid is used before, during or afterwards the mechanical thrombectomy (this is, to the patient being treated with said technique). Preferably, the composition comprising uric acid is used when the patient is treated by means of mechanical thrombectomy. In the most preferred embodiment, the composition comprising uric acid is used or administered before beginning the mechanical thrombectomy and before ending the infusion of said composition the mechanical thrombectomy is started.

It is contemplated that the mechanical thrombectomy is performed with any stent known in the state of the art and suitable for use with said technique. In a preferred embodiment, the stent used in the mechanical thrombectomy is a first generation stent, more preferably, the stent used in the mechanical thrombectomy is of the type of the Merci clot retrieval device (Concentric medical, Mountain View, Calif.), the Penumbra thromboaspiration system (Penumbra, Inc. Alameda, Calif.), balloon-mounted stents, self-expanding stents and/or retrievable stents, even more preferably the stent used in the mechanical thrombectomy is a retrievable stent, for example, the retrievable stent is Solitaire (ev3 Inc., Irvine, Calif.), Trevo (Concentric Medical, MountainView, Calif.), Solitaire FR, Pulse (Penumbra, Inc., Alameda, Calif.) or Revive (Codman Neurovascular, San Jose, Calif.). In the most preferred embodiment, the stent used in the mechanical thrombectomy is the retrievable stent Solitaire (ev3 Inc., Irvine, Calif.).

It is contemplated that the composition comprising uric acid is used alone or in combination with other compounds.

In a preferred embodiment, the composition comprising uric acid is used in combination with a thrombolytic agent, more preferably with a tissue plasminogen activator (hereinafter, tPA) (for example, alteplase).

It is also contemplated that the composition comprising uric acid is used in combination with, for example, citicoline.

In connection with what has been pointed out, it is contemplated that the combined use is within the same composition (this is, that the composition comprising uric acid additionally comprises other components such as tPA, citicoline or combinations thereof) or in the form of at least one additional composition. In the latter, it is contemplated that the composition comprising uric acid is administered before, at the same time or afterwards that the at least one additional composition.

In a preferred embodiment, the composition comprising uric acid is used in combination with a composition comprising tPA (preferably, alteplase) and both compositions are used jointly, this is, they are administered jointly, more preferably, firstly the composition comprising tPA is administered and, before finalizing the administration thereof the administration of the composition comprising uric acid is started.

The amount of uric acid in the composition is a therapeutically effective amount.

In a preferred embodiment, the dose or amount of uric acid is between 250 mg and 1250 mg, more preferably the dose or amount of uric acid is between 500 mg and 1000 mg, even more preferably the dose or amount of uric acid is 1000 mg.

In another preferred embodiment, the concentration of uric acid in the composition is between 1 mg/ml and 4 mg/ml, more preferably 2 mg/ml.

It is contemplated that the uric acid comprised in the composition, is obtained, generated or produced in accordance with any of the methods known in the state of the art. In a preferred embodiment, the uric acid is obtained by chemical synthesis.

The composition comprising uric acid can be presented in any pharmaceutically acceptable form and adapted to the elected route of administration. In this sense, the composition comprising uric acid can comprise pharmaceutically acceptable vehicles and excipients known in the state of the art. In a preferred embodiment, the composition comprising uric acid comprises a pharmaceutically acceptable liquid vehicle, more preferably said liquid vehicle is physiological serum and, even more preferably, said physiological serum comprises 0.1% of lithium carbonate and 5% mannitol.

It is contemplated that the composition comprising uric acid is a slow release composition, an immediate release composition or combinations thereof.

The composition comprising uric acid (and any of the optional at least one additional composition mentioned previously) can be administered by any of the routes known in the state of the art. In a preferred embodiment, the composition comprising uric acid is administered intravenously.

In a final aspect, the present invention refers to a method for the treatment of a patient suffering brain stroke comprising administering a composition comprising uric acid, characterized in that the patient is a brain stroke patient treated by means of mechanical thrombectomy and in that the treatment provides for synergistic effect in the treatment for brain stroke.

It is contemplated that the brain stroke is ischemic or haemorrhagic. In a preferred embodiment, the brain stroke is an ischemic brain stroke.

It is contemplated that the composition comprising uric acid is used in the method of the present invention before, during or afterwards the mechanical thrombectomy (this is, to the patient being treated with said technique). Preferably, the composition comprising uric acid is used when the patient is treated by means of mechanical thrombectomy. In the most preferred embodiment, in the method of the present invention the composition comprising uric acid is used or administered before beginning the mechanical thrombectomy and before ending the infusion of said composition the mechanical thrombectomy is started.

It is contemplated that the mechanical thrombectomy is performed with any stent known in the state of the art and suitable for use with said technique. In a preferred embodiment, the stent used in the mechanical thrombectomy is a first generation stent, more preferably, the stent used in the mechanical thrombectomy of the type of the Merci clot retrieval device (Concentric medical, Mountain View, Calif.), the Penumbra thromboaspiration system (Penumbra, Inc. Alameda, Calif.), balloon-mounted stents, self-expanding stents and/or retrievable stents, even more preferably the stent used in the mechanical thrombectomy is a retrievable stent, for example, the retrievable stent is Solitaire (ev3 Inc., Irvine, Calif.), Trevo (Concentric Medical, MountainView, Calif.), Solitaire FR, Pulse (Penumbra, Inc., Alameda, Calif.) or Revive (Codman Neurovascular, San Jose, Calif.). In the most preferred embodiment, the stent used in the mechanical thrombectomy is the retrievable stent Solitaire (ev3 Inc., Irvine, Calif.).

It is contemplated that the composition comprising uric acid is used alone or in combination with other compounds. In a preferred embodiment, the composition comprising uric acid is used in combination with a thrombolytic agent, more preferably with a tissue plasminogen activator (hereinafter, tPA) (for example, alteplase).

It is also contemplated that the composition comprising uric acid is used in combination with, for example, citicoline.

In connection with what has been pointed out, it is contemplated that the combined use is within the same composition (this is, that the composition comprising uric acid additionally comprises other components such as tPA, citicoline or combinations thereof) or in the form of at least one additional composition. In the latter, it is contemplated that the composition comprising uric acid is administered before, at the same time or afterwards that the at least one additional composition.

In a preferred embodiment, in the method of the present invention the composition comprising uric acid is used in combination with a composition comprising tPA (preferably, alteplase) and both compositions are used jointly, this is, they are administered jointly, more preferably, firstly the composition comprising tPA is administered and, before finalizing the administration thereof the administration of the composition comprising uric acid is started.

The amount of uric acid in the composition is a therapeutically effective amount.

In a preferred embodiment, the dose or amount of uric acid used in the method of the present invention is between 250 mg and 1250 mg, more preferably the dose or amount of uric acid is between 500 mg and 1000 mg, even more preferably the dose or amount of uric acid is 1000 mg.

In another preferred embodiment, the concentration of uric acid in the composition used in the method of the present invention is between 1 mg/ml and 4 mg/ml, more preferably 2 mg/ml.

It is contemplated that the acid uric comprised in the composition, is obtained, generated or produced in accordance with any of the methods known in the state of the art. In a preferred embodiment, the uric acid is obtained by chemical synthesis.

The composition comprising uric acid can be presented in any pharmaceutically acceptable form and adapted to the elected route of administration. In this sense, the composition comprising uric acid can comprise pharmaceutically acceptable vehicles and excipients known in the state of the art. In a preferred embodiment, the composition comprising uric acid comprises a pharmaceutically acceptable liquid vehicle, more preferably said liquid vehicle is physiological serum and, even more preferably, said physiological serum comprises 0.1% of lithium carbonate and 5% mannitol.

It is contemplated that the composition comprising uric acid is a slow release composition, an immediate release composition or combinations thereof.

The composition comprising uric acid (and any of the optional at least one additional composition mentioned previously) can be administered by any of the routes known in the state of the art. In a preferred embodiment, the composition comprising uric acid is administered intravenously.

To allow a better understanding, the present invention is describe hereinafter with further detail with reference to the enclosed FIGURE, that is presented as an example, and with reference to the illustrative and non-limitative example included below.

FIG. 1 shows the distribution of patients in accordance to the different scores of the mRS scale for the group treated with uric acid (top bar) and for the placebo group (bottom bar). The x axis shows the percentage of patients. In each of the boxes of the two bars in is noted: in the first line the score of the mRS scale to which the box corresponds; and the second line, firstly the number of patients of the group classified within said mRS score and, in parentheses, the percentage that said number represents with regard to the total of the group.

EXAMPLES

Example 1. Treatment with uric acid of ischemic brain stroke patients treated with intravenous thrombolysis and mechanical thrombectomy.

In total, 45 ischemic brain stroke patients were enrolled in this study and received the combination of thrombolytic treatment (using rt-PA) and mechanical thrombectomy. Of said 45 patients, randomly, 24 were assigned to the uric acid group and, hence, also received treatment with uric acid; and 21 were assigned to the placebo group that, instead of the treatment with uric acid, received physiologic serum comprising 0.1% of lithium carbonate and 5% of mannitol. The patients of this study were recruited at eight centres and, in all the cases, the corresponding informed consent was obtained from the patient or its legal representative. Details of the patients of each of the groups appear summarized in table 1.

As a whole, the median age of these patients selected for the study was 74 years (IQR of 11), 27 (60%) were men, the baseline or initial NIHSS score was 17 (12-20), and the median time from onset of the brain stroke to groin puncture was 200 (160-256) minutes.

As can be derived from Table 1, the two randomized groups showed similar baseline or initial features in relation to the features of seriousness of the occlusion (NIHSS score), localization of the intracranial occlusions, and comparable delays between the moment of the start of the symptoms and the moment of the start of the systemic or endovascular therapy (rtPA, uric acid, placebo and/or mechanical thrombectomy). Nevertheless, the patients in the urig acid group showed a median age 10 years higher than the median of the placebo group (this shift is also reflected in the interquartilic range).

TABLE 1

Features of the patients assigned to each of the study groups.

|  | Placebo (n = 21) | Uric acid (n = 24) |
|---|---|---|
| Age in years, median (interquartilic range, hereinafter IQR) | 68 (64-76) | 78 (70-80) |
| Men, n (%) | 14 (67) | 13 (54) |
| Hypertension, n (%) | 14 (67) | 15 (63) |
| Dyslipidemia, n (%) | 9 (43) | 11 (46) |
| Diabetes mellitus, n (%) | 3 (14) | 2 (8) |
| Atrial fibrillation, n (%) | 2 (10) | 11 (46) |
| Previous stroke, n (%) | 0 (0) | 2 (8) |
| Systolic blood pressure in mm Hg, mean (standard deviation, hereinafter SD) | 149 (29) | 142 (23) |
| Diastolic blood pressure in mm Hg, mean (SD) | 78 (13) | 80 (13) |
| Pretreatment glucose mg/dl, median (IQR) | 114 (107-138) | 120 (111-135) |
| NIHSS score at randomization, median (IQR) | 15 (10-20) | 17 (13-20) |
| Time from onset of the brain stroke until the treatment with rtPA in min, median (IQR) | 110 (93-145) | 115 (100-136) |
| Time from onset of the brain stroke until the tresatment with uric acid or placebo in min, median (IQR) | 153 (128-182) | 140 (115-186) |
| Time from onset of the brain stroke until the groin puncture in min, median (IQR) | 186 (155-230) | 205 (163-271) |
| Occlusion at baseline |  |  |
| ICT-T | 0 | 3 (13) |
| M1 | 11 (55) | 16 (67) |
| M2 | 4 (20) | 3 (13) |
| Tandem | 5 (25) | 1 (4) |
| Basilar | 0 | 1 (4) |

All patients that were selected for the study received one standard dose (0.9 mg/kg/h) of rtPA (in the present case, intravenous alteplase) within the 4.5 hours following the brain stroke. During infusion of intravenous alteplase, patients were assigned randomly in a 1:1 proportion to the uric acid group or to the placebo group, so that they received 500 ml of intravenous solution of 1000 mg of uric acid or placebo (physiologic serum comprising 0.1% lithium carbonate and 5% mannitol), respectively, both contained in glass bottles covered with opaque yellow bags tag in identical manner. Said treatment with uric acid or placebo was applied during 90 minutes.

In all patients by means of CT-angiography (hereinafter, CTA) showed an ICA (distal internal carotid artery), MCA-M1 (initial segment of the middle cerebral artery), or an ICA/MCA-M1 occlusion. Hence, the treatment with the intravenous alteplase (and uric acid or placebo) was followed by a mechanical thrombectomy using the retrievable stent Solitaire (ev3 Inc., Irvine, Calif.). The mechanical thrombectomy procedure was carried in accordance to the procedure pointed out in the REVASCAT assay (Jovin T G, Chamorro A, Cobo E, de Miguel M A, Molina C A, Rovira A, San Román L, Serena J, Abilleira S, Ribó M, Millán M, Urra X, Cardona P, López-Cancio E, Tomasello A, Castaño C, Blasco J, Aja L, Dorado L, Quesada H, Rubiera M, Hernandez-Pérez M, Goyal M, Demchuk A M, von Kummer R, Gallofré M, Dávalos A; REVASCAT Trial Investigators.. Thrombectomy within 8 hours after symptom onset in ischemic stroke. N Engl J Med. 2015; 372:2296-306) and it was started before the 90 minutes of the infusion of the composition with uric acid or placebo had elapsed.

To determine if the revascularization was successful the conventional technique of digital angiography by subtraction was used. Successful vessel revascularization was considered that with grade 2b (indicating reperfusion of from 50% to 90% of the damaged zone), or grade 3 (complete reperfusion of the damaged zone) in accordance with the modified Thrombolysis in Cerebral Infarction (hereinafter, mTICI) scale of 0 to 3. The results obtained are shown in table 2, from which it can be derived that no significant differences could be observed between said two groups regarding successfulness in the revascularization. Also, no differences were observed in revascularization with regard to the observed in the state of the art in the use of mechanical thrombectomy (Jovin et al. N Engl J Med. 2015; 372:2296-306).

TABLE 2

Summary of the results obtained in the measurement of successfulness in revascularization in accordance with conventional angiography techniques. In the last row of the table the counting of the two scores considered as successful revascularization, this is 2b and 3, is included.

| mTICI Score | Placebo (n = 21) | Uric acid (n = 24) | P value |
|---|---|---|---|
| 0 | 1 (5) | 3 (13) | 0.39 |
| 1 | 1 (5) | 0 | 0.27 |
| 2a | 2 (10) | 1 (4) | 0.65 |
| 2b | 6 (30) | 7 (29) | 0.95 |
| 3 | 10 (50) | 13 (54) | 0.78 |
| 2b/3 | 16 (80) | 20 (83) | 0.78 |

The results of the study appear summarized in table 3 and in FIG. 1.

TABLE 3

Summary of the efficacy results of the treatment for the two study groups analysed.

|  | Placebo (n = 21) | Uric acid (n = 24) |
|---|---|---|
| mRS score of between 0-2 at 90 días, n (%) | 10 (47.6) | 16 (66.6) |
| Barthel index score of 95-100 at 90 days, n (%) | 9 (42.8) | 16 (66.6) |
| Brain stroke worsening within 72 h from the treatment, n (%) | 4 (19) | 0 |
| NIHSS score 0 at 90 days, n (%) | 6 (28.6) | 9 (37.5) |
| Volume of the infarcted zone at 72 hours of the treatment measured by means of magnetic resonance image of the | 28.4 (35.3) | 17.2 (15.5) |

TABLE 3-continued

Summary of the efficacy results of the treatment for the two study groups analysed.

|  | Placebo (n = 21) | Uric acid (n = 24) |
|---|---|---|
| brain, mean (SD) Growth of the infarcted zone at 72 hours of the treatment ml, mean (SD) | −0.7 (30.0) | −33.2 (22.3) |

As can be derived from table 3, the group treated with uric acid show an statistically significant and surprising improvement in: the measurement of good results at 90 days (mRS score of between 0-2 at 90 dias), complete independence of the patients at 90 days (Barthel index score of 95-100 at 90 days) and growth of the infarcted zone at 72 hours from the treatment. Additionally, a positive and improvement tendency in the rest of measured parameters was seen.

The same type of study was carried out with other subpopulations with ischemic brain stroke (not treated with mechanical thrombectomy, but the rest of the treatment and the procedure was the same). Results appear summarized in tables 4 and 5:

TABLE 4

Summary of the efficacy results of the treatment carried out in the general population of patients with ischemic brain stroke not treated with mechanical thrombectomy.

|  | Placebo (n = 179) | Uric acid (n = 187) |
|---|---|---|
| mRS score of between 0-2 at 90 dies, n (%) | 95 (50.8) | 80 (44.7) |
| Barthel index score of 95-100 at 90 days, n (%) | 72 (40.2) | 86 (45.6) |

TABLE 5

Summary of the efficacy results of the treatment carried out in different subgroups of population with ischemic brain stroke not treated with mechanical thrombectomy.

| Population subgroup Patients with hypertension (condition defined as: arterial pressure over 160 mmHg) (n = 251) | Study group | |
|---|---|---|
|  | Placebo (n = 120) | Uric acid (n = 131) |
| mRS score of between 0-2 at 90 dies, n (%) | 45 (37.5) | 68 (48.9) |
| Barthel index score of 95-100 at 90 days, n (%) Patients with diabetes (n = 113) | 42 (35) | 60 (45.8) |
|  | Placebo (n = 58) | Uric acid (n = 55) |
| mRS score of between 0-2 at 90 dies, n (%) | 20 (34.5) | 25 (45.5) |
| Barthel index score of 95-100 at 90 days, n (%) Patients with atrial fibrillation (n = 77) | 42 (35) | 60 (45.8) |
|  | Placebo (n = 42) | Uric acid (n = 35) |
| mRS score of between 0-2 at 90 dies, n (%) | 13 (31) | 15 (42.9) |
| Barthel index score of 95-100 at 90 days, n (%) | 12 (28.6) | 11 (31.4) |

TABLE 5-continued

Summary of the efficacy results of the treatment carried out in different subgroups of population with ischemic brain stroke not treated with mechanical thrombectomy.

| Population subgroup Patients with hypertension (condition defined as: arterial pressure over 160 mmHg) (n = 251) | Study group | |
|---|---|---|
| Patients which have suffered previous brain stroke (n = 47) | | |
|  | Placebo (n = 17) | Uric acid (n = 30) |
| mRS score of between 0-2 at 90 dies, n (%) | 6 (35.3) | 13 (43.3) |
| Barthel index score of 95-100 at 90 days, n (%) Men patients (n = 178) | 7 (41.2) | 12 (40) |
|  | Placebo (n = 91) | Uric acid (n = 87) |
| mRS score of between 0-2 at 90 dies, n (%) | 44 (48.4) | 45 (51.7) |
| Barthel index score of 95-100 at 90 days, n (%) Women patients (n = 188) | 41 (45.1) | 44 (50.6) |
|  | Placebo (n = 88) | Uric acid (n = 100) |
| mRS score of between 0-2 at 90 dies, n (%) | 36 (40.9) | 50 (50) |
| Barthel index score of 95-100 at 90 days, n (%) Smoking patients (n = 60) | 31 (35.2) | 42 (42) |
|  | Placebo (n = 25) | Uric acid (n = 35) |
| mRS score of between 0-2 at 90 dies, n (%) | 14 (38.2) | 21 (50) |
| Barthel index score of 95-100 at 90 days, n (%) Patients with dyslipidaemia (n = 148) | 11 (44) | 15 (42.9) |
|  | Placebo (n = 67) | Uric acid (n = 81) |
| mRS score of between 0-2 at 90 dies, n (%) | 25 (37.3) | 40 (49.4) |
| Barthel index score of 95-100 at 90 days, n (%) Patients with coronary disease (n = 157) | 23 (34.3) | 41 (50.6) |
|  | Placebo (n = 24) | Uric acid (n = 31) |
| mRS score of between 0-2 at 90 dies, n (%) | 8 (33.3) | 14 (45.2) |
| Barthel index score of 95-100 at 90 days, n (%) Patients with large vessel arteriosclerosis (arterial stenosis +2250%) (n = 46) | 8 (33.3) | 16 (51.6) |
|  | Placebo (n = 27) | Uric acid (n = 19) |
| mRS score of between 0-2 at 90 dies, n (%) | 11 (40.7) | 6 (31.6) |
| Barthel index score of 95-100 at 90 days, n (%) Patients with cardioembolism (n = 157) | 10 (37) | 4 (21.1) |
|  | Placebo (n = 71) | Uric acid (n = 86) |
| mRS score of between 0-2 at 90 dies, n (%) | 32 (45.1) | 42 (48.8) |
| Barthel index score of 95- | 29 (40.8) | 39 (45.3) |

TABLE 5-continued

Summary of the efficacy results of the treatment carried out in different subgroups of population with ischemic brain stroke not treated with mechanical thrombectomy.

Population subgroup
Patients with hypertension
(condition defined as:
arterial pressure over 160
mmHg) (n = 251)                                   Study group 100 at 90 days, n (%)
Patients which consume
alcohol (n = 23)

|  | Placebo (n = 13) | Uric acid (n = 10) |
| --- | --- | --- |
| mRS score of between 0-2 at 90 dies, n (%) | 9 (69.2) | 4 (40) |
| Barthel index score of 95-100 at 90 days, n (%) | 8 (61.2) | 2 (20) |

The results obtained show a synergistic and surprisingly increased effect of the use of uric acid in the group of brain stroke patients with mechanical thrombectomy. As seen in table 4, in the general population (not including the subgroup of brain stroke patients with mechanical thrombectomy), the uric acid did not show a detectable effect in the percentage of patients with an mRS score of between 0 and 2 at 90 days. Additionally, as can be seen in said table, the uric acid also showed only a minimal effect in the percentage of patients with Barthel index score 95-100. Nevertheless, as can be seen in table 3, the use of uric acid in the group of patients of brain stroke with mechanical thrombectomy, said uric acid exceedingly increases its effect and is able to significantly and very appreciably improve the result in the patients.

Additionally, as can be derived from table 5, in any other of the analysed groups of patients of brain stroke, the uric acid shows a synergistic and so high effect of the two parameters mentioned above.

The increase observed in the treatment with uric acid in the present study is even more surprising and reflects even more a synergistic effect in the treatment of the specific subgroup of patients, if we take into account that the patients selected in the present study are patients with worse prognosis (they are those with occlusion of a larger artery), and therefore, it would be expected that in these patients, the effect of uric acid was lower than that observed in patients with a less serious cerebral infarct (for example, patients of the URICO-ICTUS study)

In addition, certain parameters (death, incidence of intracranial hemorrhages and incidence of gout attacks) were measured in order to determine the safety of the new treatment (treatment of the present invention). It was found that no differences were observed between the analysed groups (uric acid group and placebo group) in any of the variables measured in relation to the safety of the treatment of the present invention. Thus, the treatment of the present invention proved to be safe, in addition to, as noted above, surprisingly effective.

Therefore, as demonstrated in this example, uric acid combined with mechanical thrombectomy, applied to patients with cerebral infarction, act synergistically increasing the positive effects observed in patients.

The invention claimed is:

1. A method for the treatment of a patient suffering brain stroke comprising:
   administering a composition comprising uric acid; and
   carrying out a mechanical thrombectomy procedure before, during or after a time for the administration of the composition comprising uric acid has elapsed,
   wherein the treatment provides for synergistic effect in the treatment for brain stroke.

2. The method in accordance with claim 1, wherein the brain stroke is an ischemic brain stroke.

3. The method in accordance with claim 1, wherein the composition comprising uric acid is used in combination with a composition comprising a thrombolytic agent.

4. The method in accordance with claim 3, wherein the thrombolytic agent is alteplase.

5. The method in accordance with claim 1, wherein the composition comprising uric acid additionally comprises citicoline.

6. The method in accordance with claim 1, wherein the dose of uric acid is between 250 mg and 1250 mg.

7. The method in accordance with claim 6, wherein the dose of uric acid is 1000 mg.

8. The method in accordance with claim 1, wherein the uric acid concentration in the composition is between 1 mg/ml and 4 mg/ml.

9. The method in accordance with claim 8, wherein the concentration of uric acid in the composition is 2 mg/ml.

10. The method in accordance with claim 1, wherein the composition comprising uric acid is administered intravenously.

11. The method in accordance with claim 1, wherein the time for the administration of the composition comprising uric acid is 90 minutes.

12. The method in accordance with claim 3, wherein the step of administering the thrombolytic agent is carried out within about 4.5 hours following the brain stroke.

13. The method in accordance with claim 1, wherein prior to administering the composition comprising uric acid, a thrombolytic agent is administered.

* * * * *